US008167615B2

(12) United States Patent
Jacotti

(10) Patent No.: US 8,167,615 B2
(45) Date of Patent: May 1, 2012

(54) MANUFACTURING METHOD FOR A GUIDING TEMPLATE FOR DENTAL IMPLANTOLOGY

(75) Inventor: Michele Jacotti, Brescia (IT)

(73) Assignee: Studio Dentistico Dr. Jacotti Michele, Brescia (IT)

( * ) Notice: Subject to any disclaimer, the term of this patent is extended or adjusted under 35 U.S.C. 154(b) by 201 days.

(21) Appl. No.: 12/533,124

(22) Filed: Jul. 31, 2009

(65) Prior Publication Data

US 2010/0028826 A1      Feb. 4, 2010

Related U.S. Application Data

(63) Continuation of application No. PCT/IT2007/000861, filed on Dec. 11, 2007.

(30) Foreign Application Priority Data

Mar. 26, 2007   (IT) .............................. BS2007A0040

(51) Int. Cl.
*A61C 3/00*           (2006.01)
(52) U.S. Cl. ........................................................ 433/75
(58) Field of Classification Search ................... 433/75, 433/76, 172; 600/589, 590
See application file for complete search history.

(56) References Cited

U.S. PATENT DOCUMENTS

| 7,574,025 | B2 * | 8/2009 | Feldman ........................ 382/128 |
| 2002/0160337 | A1 | 10/2002 | Klein et al. |
| 2006/0105291 | A1 * | 5/2006 | Stein et al. ...................... 433/75 |
| 2006/0281046 | A1 * | 12/2006 | Heo ............................... 433/75 |

FOREIGN PATENT DOCUMENTS

WO    WO 2007/022995 A1    3/2007

OTHER PUBLICATIONS

Notification of Transmittal of the International Search Report and the Written Opinion of the International Search Authority, or the Declaration, International Search Report, and Written Opinion of the International Search Authority issued in corresponding International Patent Application No. PCT/IT2007/000861 dated May 21, 2008 (13 pages).

* cited by examiner

*Primary Examiner* — John J Wilson
(74) *Attorney, Agent, or Firm* — Kilyk & Bowersox, P.L.L.C.

(57) ABSTRACT

The present invention relates to a method for making a guiding template for dental implantation. The method provides for associating a base template to a reference device, subjecting the patient to CAT, loading the data to a computer program, making an implant planning, generating the volume model, coupling the volume model to the reference device model, projecting the elements of the implant planning on the volume model, making a volume suitably drilled on the basis of the projection, coupling the volume to the reference device and making the holes of the planning on the base template. The present invention also relates to the guiding template thus obtained and the reference device for carrying out the method.

9 Claims, 4 Drawing Sheets

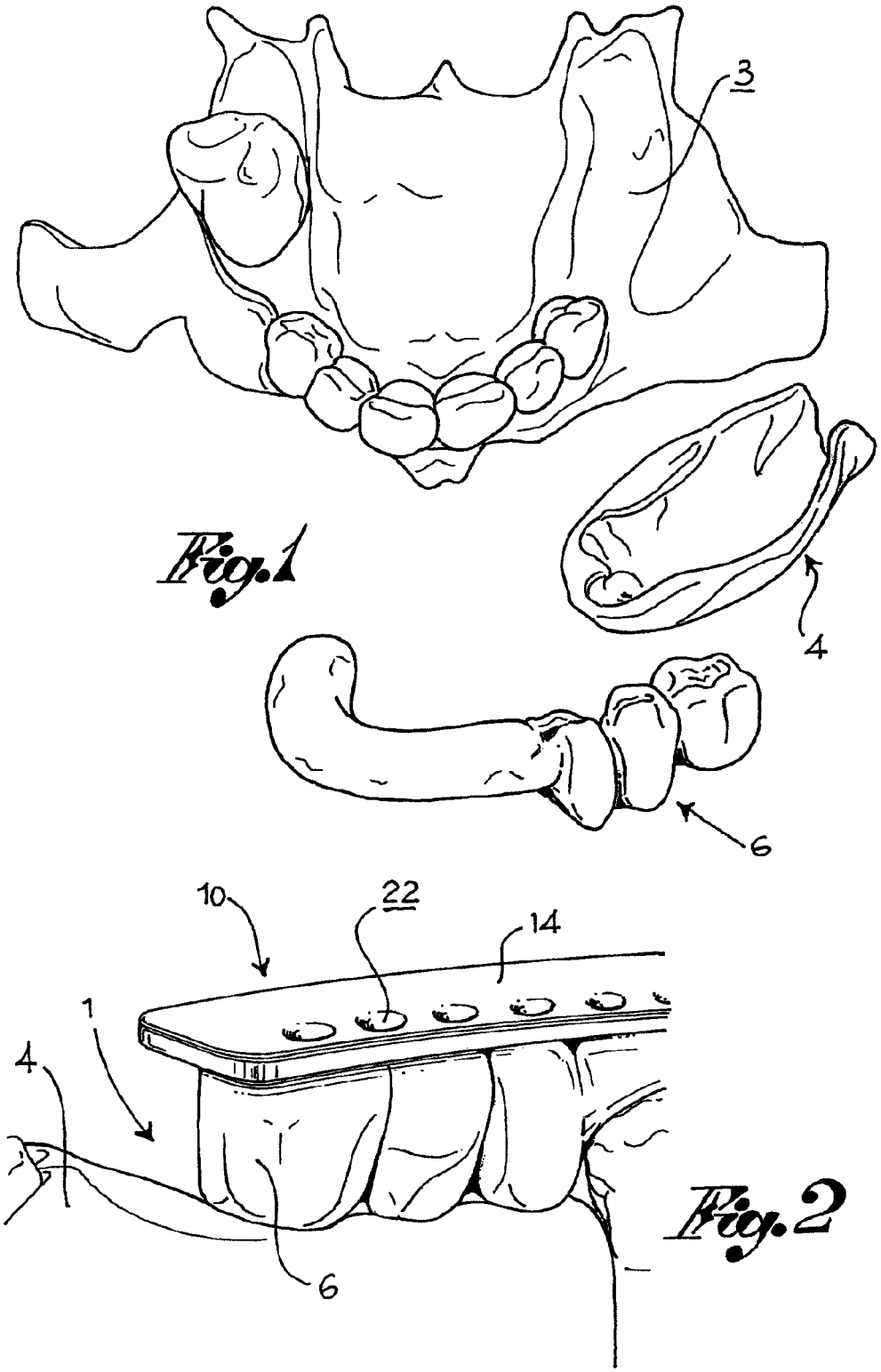

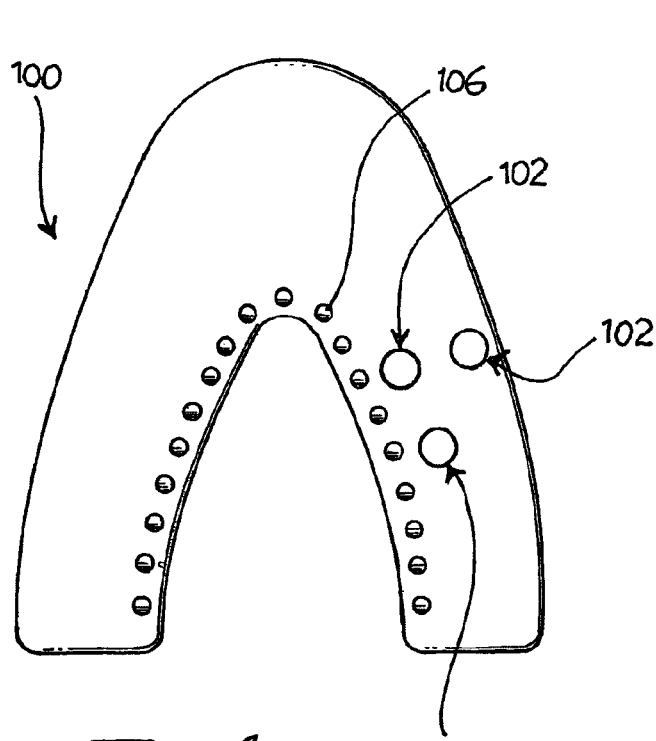
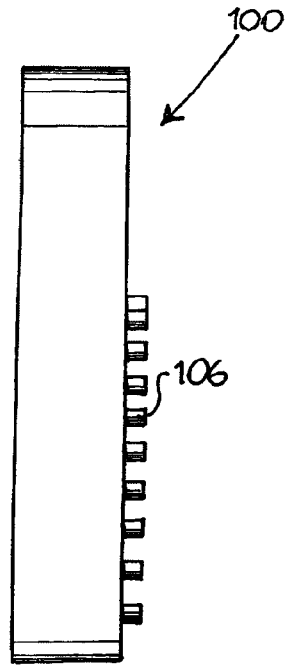
Fig. 4a　　　Fig. 4b
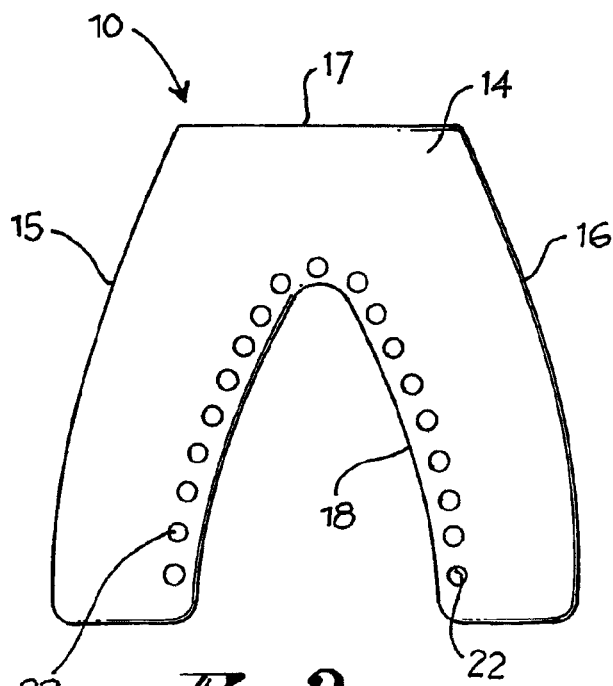
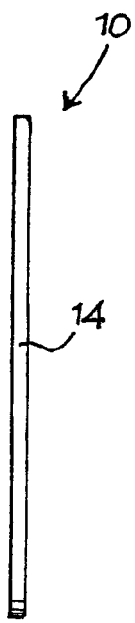
Fig. 3a　　　Fig. 3b

MANUFACTURING METHOD FOR A GUIDING TEMPLATE FOR DENTAL IMPLANTOLOGY

This application is a continuation of International Patent Application No. PCT/IT2007/000861, filed Dec. 11, 2007, which claims priority from Italian Patent Application No. BS2007A000040, filed Mar. 26, 2007, and are incorporated in their entirety by reference herein.

FIELD OF THE INVENTION

The present invention relates to a method for making a surgical template, in particular for dental implantation.

BACKGROUND OF THE INVENTION

As it is known, dental implantation allows implanting one or more reconstructed teeth in place of missing teeth, obtaining a result that is often excellent from the aesthetic point of view, since the reconstructed teeth virtually cannot be made out from original healthy teeth.

A set for dental implant comprises a reconstructed tooth and an implant, that is, a sort of pin, intended to be implanted in the bone of the mandibular body or of the maxillary body, protruding from the gum at the vacant seat of the missing tooth, to allow fixing the reconstructed tooth.

It is understood that the implant arrangement (position of the axis thereof, inclination, etc.) has a fundamental importance, as it must be introduced in the bone keeping into due account the shape thereof and avoiding interference with interested anatomical structures.

For this reason, before implanting the implant, a hole is made in the bone wherein the implant, generally self-threading, is then inserted.

The hole is made by a miller guided by a guiding template which generally couples with shape coupling to the teeth adjacent the vacant seat and is provided with guiding holes suitably positioned on the template and suitably inclined.

As it can be understood, the manufacturing of the guiding template provided with the holes takes on a fundamental role.

Several known methods exist for making guiding templates for dental implantation.

Some of these are for example described in documents WO 95/28688 and EP-A1-1486900.

However, such methods exhibit some drawbacks, due to their execution complexity, to particularly long execution times or to the often high execution cost.

SUMMARY OF THE INVENTION

The object of the present invention is to find a method for making a guiding template for dental implantation, that meets the above requirements and overcomes the drawbacks of the prior art.

Such object is achieved by a method for making a guiding template for dental implantation, comprising the steps of:

making a base template suitable for being coupled to one or more teeth of the dental arch;

associating the base template to a reference device, making a reference assembly;

removably associating the reference set to the dental arch;

obtaining a model of the reference set associated to the dental arch through scanning devices and processing programs, the model consisting of the model of at least a portion of the dental arch, the model of at least a portion of the base template and the model of at least a portion of the reference device, coupled to one another;

determining a model of construction elements relating to an implant planning on the dental arch model;

generating a volume model;

coupling the volume model to the reference device model;

determining a model of guiding elements on the volume model, generated based on the model of construction elements determined on the model of the arch;

obtaining a volume based on the volume model and guiding elements thereon based on the model of guiding elements;

coupling the volume to the reference device of the reference set;

making construction elements on the base template based on the guiding elements of the volume, thus obtaining the guiding template.

BRIEF DESCRIPTION OF THE DRAWINGS

FIG. 1 shows a set comprising a mandibular body and the coupling portion and the reconstructed portion of a base template.

FIG. 2 shows a reference set coupled to the dental arch.

FIGS. 3a and 3b show two views of a reference device according to the present invention.

FIGS. 4a and 4b show two views of a volume according to the present invention.

DETAILED DESCRIPTION OF THE INVENTION

Figure 5:
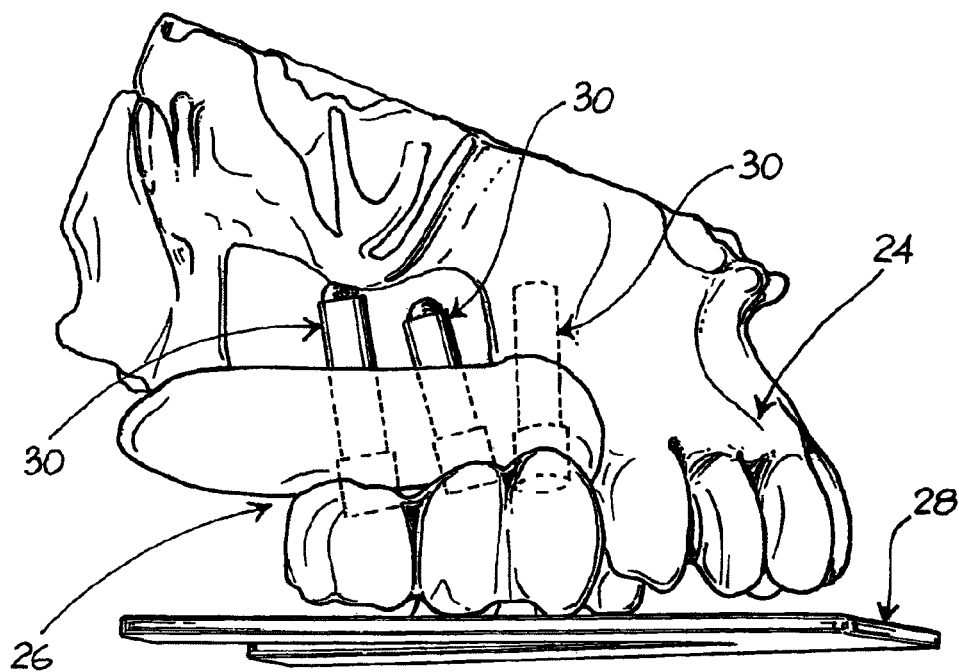
FIGS. 5 to 8 show the displays that may be obtained from a processor program as regards some steps of the method according to the present invention.

For clarity of description, in the following description reference shall be made to the case of a single tooth missing in the mandibular dental arch, for whom it is necessary to implant an implant in the mandibular body bone so as to fix thereto a reconstructed tooth, which will position in the seat left vacant by the missing tooth.

However, it is understood that the method may be carried out without inventive efforts even in the case of multiple missing teeth and with reference to the jaw dental arch, as in the case of total edentulism.

The method according to the present invention envisages the step of making a base template 1 suitable for being coupled to one or more residual teeth of the dental arch 2, in general adjacent a vacant seat 3 of the missing tooth, or suitable to be positioned on the gums.

Preferably, the base template 1 comprises a coupling portion 4 suitable for coupling by shape coupling to the residual teeth (or to the gum) and a reconstructed portion 6 having the shape of the missing tooth.

Generally, the base template 1 is made of resin.

Then, the method envisages the step of associating the base template 1 to a reference device 10, making a reference assembly.

According to the present invention, the reference device 10 comprises a plate 14, generally of a plastic, biocompatible and substantially radio-opaque material, preferably plane. The plate is shaped and sufficiently thin so that the reference set may be introduced in the oral cavity while allowing the air passage for breathing.

Preferably, plate 14 exhibits a horseshoe plan that substantially imitates the pattern of the dental arch. The plate is more elongated in a direction, coinciding with that of insertion in the oral cavity, than in the other, perpendicular thereto.

For example, plate 14 exhibits an outer edge consisting of a first arched side 15 and a second arched side 16, symmetrical to the first one relative to the direction of insertion in the oral cavity, jointed at the front by a rectilinear side 17, arranged substantially perpendicular to the direction of insertion. The plate further exhibits an inner edge 18, also arched and of semi-elliptical shape but sharp, recessing towards the rectilinear side 17 of the outer edge.

In use, plate 14 is intended to be introduced in the oral cavity together with the base template, so that the outer edge faces outwards of the oral cavity. By virtue of the recess of the inner edge 18 towards the outer one, a passage is made, useful for the breathing air passage.

Plate 14 exhibits first reference means suitable for defining predetermined positions on the plate itself.

For example, the reference means comprise a plurality of holes 22, distributed on at least one of the plate surfaces, preferably passing through the thickness thereof.

Preferably, the holes are positioned peripherally to plate 14, for example bordering the inner edge 18.

In an embodiment variation, the reference means comprise a plurality of projections.

The method according to the present invention further provides the step of associating the reference set to the dental arch.

In other words, the base template 1, and in particular the reconstructed portion 6 thereof, is associated to plate 14, for example glued, and introduced in the patient's oral cavity, so that the coupling portion of the base template couples with the adjacent teeth or rests on the gums.

Usually, plate 14 is glued at the head to the reconstructed portion 6 that simulates the teeth to be implanted, so there are no problems of interference of plate 14 into the oral cavity, since the plate arranges surmounting the teeth.

After that, the method according to the present invention provides the step of obtaining, through scanning devices, a model of the reference set associated to the dental arch (FIG. 5).

The set assembly consists on the model of at least a portion of the dental arch 24, on the model of at least a portion of the guiding template 26 and on the model of at least a portion of the reference device 28, coupled to one another.

Within the present application, the term "model" refers to a representation of a physical object, obtained by a computer program, for example by a computerised graphic program.

For example, the term "model of the reference set associated to the dental arch" refers to the computerised representation of the reference set associated to the dental arch.

The model can be obtained through scanning devices, for example by a computerised tomograph capable of making a computerized tomography or a computerized axial tomography (CAT).

The scanning devices generate a plurality of pieces of information that provided to a computer program, originate the representation of the reference set associated to the dental arch.

In other words, the patient provided with the reference set inserted in the oral cavity and properly positioned, so that the coupling portion 4 is well coupled to the teeth adjacent the vacant seat 3 or well resting on the gum, is subjected to a CAT. The information obtained by the CAT are provided to a computer program, capable of processing them for obtaining the model of the reference set coupled to the dental arch or a portion thereof, on the display.

After that, the method according to the present invention provides the step of determining on the dental arch model, a model of construction elements relating to an implant planning (FIG. 5).

In other words, using the computer program, the implantologist makes an implant planning on the dental arch model following the indications of the model of the base template 26.

During the implant planning, the computer program generates for example an implant model 30, that the implantologist provides to arrange properly relative to the model of the dental arch 24 and of the base template 26, thus keeping into account the desired result, the patient's bone shape and the anatomical parts.

Arranging the implant model 30 means, in particular, positioning the implant in a predetermined position relative to the model of the dental arch 24 and of the base template 26 and suitably inclining the axis thereof.

The term "model of construction elements" indicates the computerised representation of the construction elements designed during the implant planning, that is, the computerised representation of the implant models 30 designed, provided with a position, an inclination and a depth.

Figure 6:
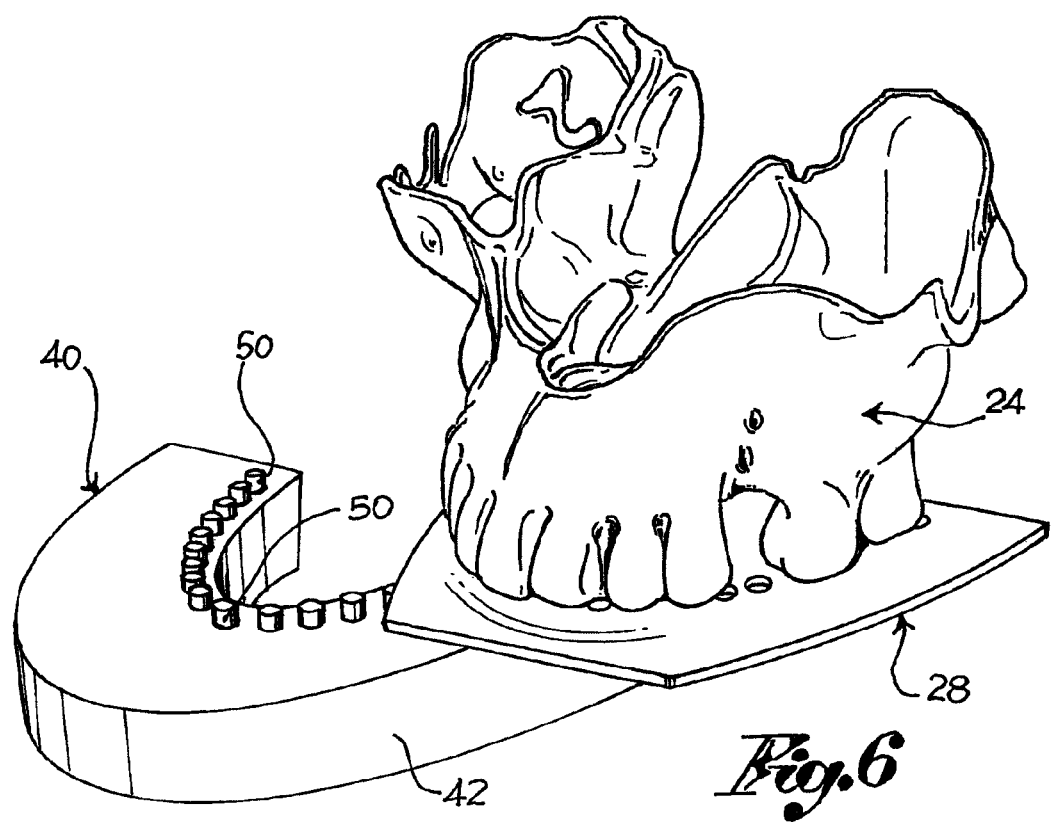

After that, the method according to the present invention provides the step of generating a volume model 40 (FIG. 6).

The volume model 40 consists of the representation of a body 42 preferably having a shape similar to that of the reference device 10, that is, of plate 14, and therefore similar to the model of reference device 28.

Preferably, the volume model 40 comprises a model of second reference means suitable for being coupled to the model of the first reference means of the model of the reference device 28.

For example, the model of second reference means comprises a plurality of projections 50 that can be coupled to the holes of the model of reference device 28, so as to position the model of reference device 28 relative to the volume model 40.

In an embodiment variation, the second reference means comprise a plurality of holes, that can be coupled to the optional projections of the reference device.

Figure 7:
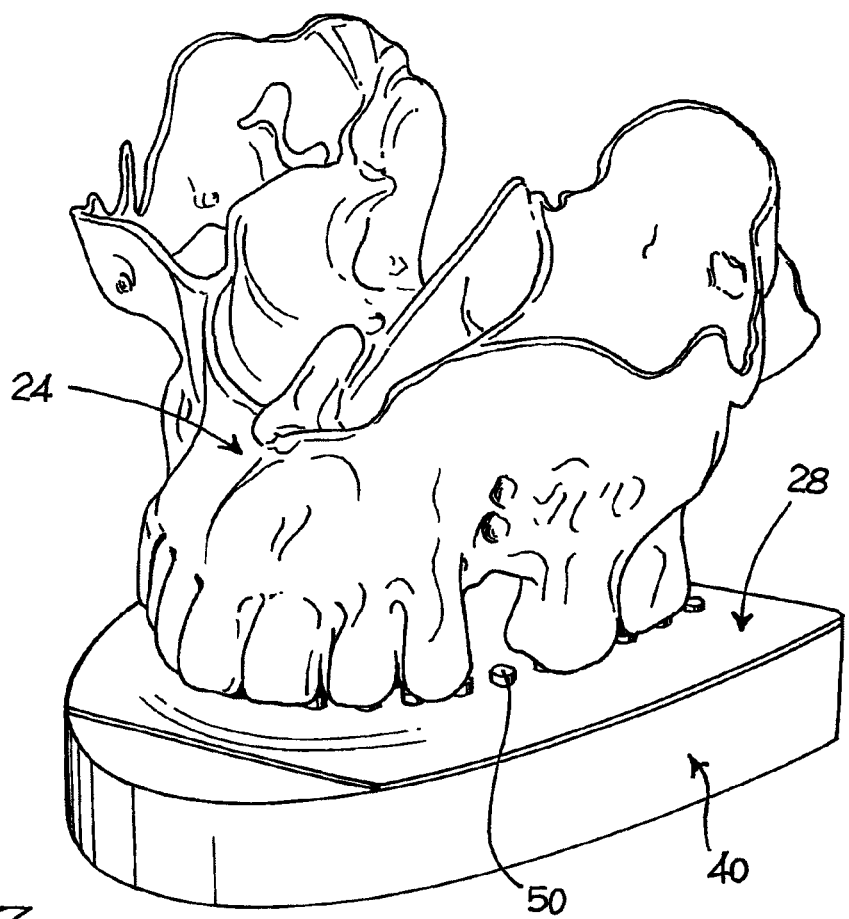

After that, the method according to the present invention comprises the step of coupling the volume model 40 to the model of reference device 28, using the model of the first reference means and the model of the second reference means (FIG. 7).

For example, some of the holes of the model of the first reference means are selected through the computer program; the computer program determines the projections of the model of the second reference means corresponding to the selected holes and processes the models of the reference device and of the volume so as to make the projections penetrate into the respective holes.

In yet other words, the volume model 40 is made to overlap the model of the reference device 28, using the holes and the projections as positioning references.

Figure 8:
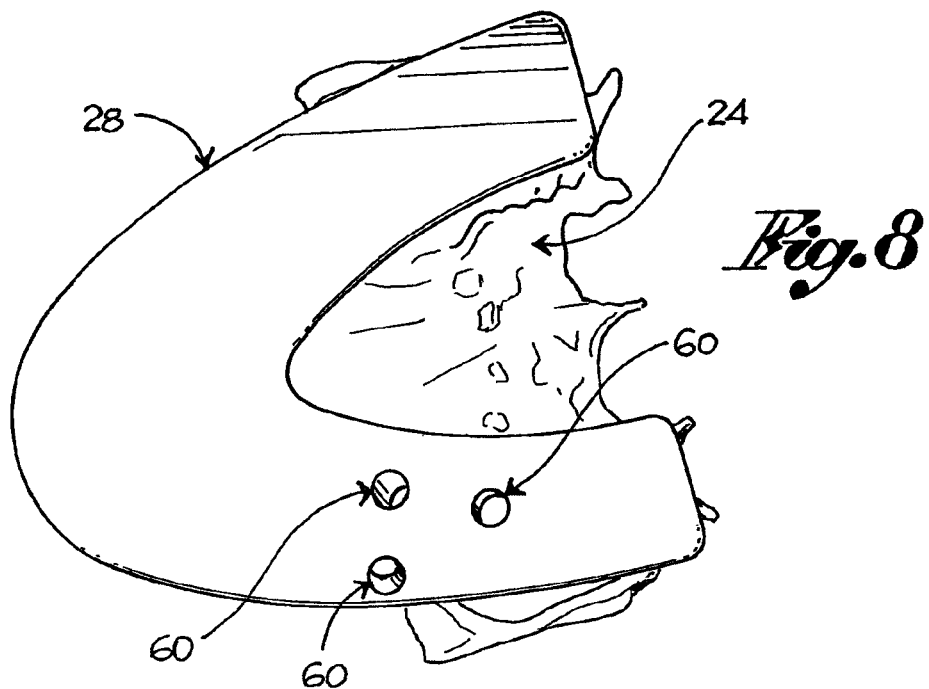

After that, the method according to the present invention provides the step of determining on the volume model 40 a model of guiding elements 60 generated based on the model of construction elements 30 determined on the model of arch 24 (FIG. 8).

In other words, the model of construction elements 30 generated during the implant planning is projected by the computer program up to intercept the volume model 40 coupled to the model of reference device 28, obtaining a model of guiding elements 60 on the volume model 40.

For example, the implant models 30 designed are projected up to intercept the volume model 40, thus making a set of holes on the volume model 40.

After that, the method according to the present invention provides the step of obtaining a volume 100 based on the volume model 40 and guiding elements 102 (holes in the illustrated case) thereon based on the model of guiding elements 60.

In other words, after having preferably separated the volume model 40 provided with the model of guiding elements 60 from the model of reference device 28, volume 100 is obtained, provided with the guiding elements 102 based on the volume model 40 and on the model of guiding elements 60.

Volume 102 further comprises second reference means, obtained thereon based on the model of second reference means 50, the second reference means being suitable for coupling to the first reference means of the reference device 10 for relatively positioning volume 100 and the reference device 10.

For example, the second reference means comprise a plurality of projections 106, corresponding to projections 50 of the volume model 40.

Preferably, the volume model 40 provided of the model of guiding elements 60 is exported by the computer program to an advanced graphic program, for example a CAD program.

Rapid prototyping techniques or CAM techniques are for example used to obtain volume 100.

In other words, a suitably drilled material volume 100 is obtained through the above techniques, wherein the holes have such arrangement and inclination that if projected on the reference device coupled to the guiding template, intercept the guiding template like the implants designed during the implant planning.

In fact, after that the method according to the present invention provides the step of coupling volume 100 provided with the guiding elements 102 to the reference device 10 of the reference set, through projections 106 that penetrate holes 22, and of making construction elements on the base template 1 based on the guiding elements of the volume, thus obtaining the guiding template.

For example, volume 100 provided with the guiding elements 102, that is the holes, is coupled to plate 14, generally inserting projections 106 of volume 100 in holes 22 of plate 14; a tool, generally a miller, is inserted through the guiding elements of the volume and made to advance progressively interfering with the plate and with the base template, drilling them.

This way, a projection of the guiding elements on the base template is obtained, which will be drilled as if it were crossed by the implants designed during the implant planning.

The base template 1 provided with holes thus obtained, that is, with the construction elements obtained based on the guiding elements, makes the guiding template.

After that, the holes of the guiding template are coated, for example with parts of a hard and biocompatible material, for example titanium.

To make the implantation on the patient, the guiding template is inserted in the oral cavity, coupled to the teeth adjacent the vacant seat of the missing tooth or resting on the gum. A revolving too, generally a miller, is inserted in the holes of the guiding template and made to advance up to drill the bone. The holes in the bone will have a position and inclination corresponding to that of the model of the implants designed in the implant planning.

A further aspect of the present invention refers to plate 14 used to make the reference set.

An even further aspect of the present invention refers to volume 100 used as a template to drill the base template.

Innovatively, the method for making a guiding template according to the present invention allows making the template in a very precise manner, that is, meeting the implant planning as designed, simple and quick.

Advantageously, moreover, the method allows using a base template of the type desired by the doctor without constraints due to the method to use for correct drilling thereof.

It is clear that a man skilled in the art may make changes and variations to the template described above.

For example, the plate may be made with a plan shape other than that illustrated, for example to adjust to the positioning in different zones of the oral cavity.

Moreover, materials other than those listed may be used.

Also such embodiments are deemed to be comprised within the scope of protection as defined by the following claims.

The invention claimed is:

1. Method for making a guiding template for dental implantation, comprising the steps of:
    making a base template suitable for being coupled to one or more teeth of the dental arch;
    associating the base template to a reference device, making a reference set;
    removably associating the reference set to the dental arch;
    obtaining a model of the reference set associated to the dental arch through scanning devices and processing programs to provide a dental arch model, the dental arch model comprising a computerized representation of at least a portion of the dental arch, the model of at least a portion of the base template and the model of at least a portion of the reference device, coupled to one another;
    determining a model of construction elements relating to an implant planning on the dental arch model, wherein the model of construction elements comprises a computerised representation of implant models used to attach a reconstructed tooth to bone, wherein the implant models are designed, provided with a position, an inclination and a depth, relative to the dental arch model and the base template;
    generating a volume model comprising a representation of a body suitable for being coupled to the reference device;
    coupling the volume model to the reference device model with computer programming;
    determining a model of guiding elements on the volume model with computer programming, generated based on the model of construction elements determined on the model of the arch;
    obtaining a volume based on the volume model and guiding elements thereon based on the model of guiding elements;
    coupling the volume to the reference device of the reference set;
    making guiding holes in the base template based on the guiding elements of the volume, wherein the guiding holes correspond to the locations and inclinations of the implant models, thus obtaining the guiding template.

2. Method according to claim 1, wherein the step of determining a model of guiding elements on the volume model comprises the step of projecting the model of construction elements intercepting the volume model.

3. Method according to claim 1, wherein the step of associating the base template to a reference device comprises the step of gluing the base template to the reference device.

4. Method according to claim 1, wherein the step of obtaining the model of the reference set associated to the dental arch comprises the step of making a computerised tomography.

5. Method according to claim 1, wherein the step of determining the model of construction elements comprises the step of generating an implant model and arranging the implant model in a desired position and according to an inclination relative to the model of the dental arch and to the model of the base template.

6. Method according to claim 1, wherein the step of coupling the volume model to the reference device model comprises the step of coupling the model of first reference means of the model of the reference assembly to the model of second reference means of the volume model.

7. Method according to claim 1, wherein the step of making the volume provided with the guiding elements comprises the step of executing a prototyping technique.

8. Method according to claim 1, wherein the step of coupling the volume to the reference device comprises the step of coupling second reference means of the volume to first reference means of the reference device.

9. Method according to claim 1, wherein the step of making guiding holes in the base template comprises the step of using a revolving drilling tool, coupling it to the volume so that the tool is guided in advancement by the guiding holes and drilling the base template.

* * * * *